United States Patent
Hilal-Alnaqbi et al.

(10) Patent No.: US 9,718,029 B2
(45) Date of Patent: Aug. 1, 2017

(54) SERVICEABLE BIOREACTOR

(71) Applicant: United Arab Emirates University, Al-Ain, Abu Dhabi (AE)

(72) Inventors: Ali Abdullah Hilal-Alnaqbi, Abu Dhabi (AE); Abdel-Hamid Ismail Mourad, Abu Dhabi (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 432 days.

(21) Appl. No.: 13/863,123

(22) Filed: Apr. 15, 2013

(65) Prior Publication Data

US 2013/0333178 A1    Dec. 19, 2013
US 2014/0310932 A2    Oct. 23, 2014

(30) Foreign Application Priority Data

Jun. 15, 2012 (GB) .................................. 1210685.2

(51) Int. Cl.
*B01D 65/02* (2006.01)
*B01D 67/00* (2006.01)
(Continued)

(52) U.S. Cl.
CPC ............... *B01D 65/02* (2013.01); *A61M 1/34* (2013.01); *A61M 1/3475* (2014.02);
(Continued)

(58) Field of Classification Search
CPC .... A61M 1/34; A61M 1/3475; A61M 1/3489; A61M 1/3496; B01D 61/28; B01D 63/00;
(Continued)

(56) References Cited

U.S. PATENT DOCUMENTS 6,242,248 B1 * 6/2001 Rozga et al. .............. 435/297.4
6,582,955 B2    6/2003 Martinez et al.
(Continued)

FOREIGN PATENT DOCUMENTS

CN          101199436 A      6/2008

OTHER PUBLICATIONS

A. Hilal-Alnaqbi, Y. Basem and J. D. S. Gaylor, "Fiber in Fiber (FIF) bioartificial liver device: initial design and prototyping", Computer-Aided Design & Applications, 8(1), 2011, pp. 99-109.

*Primary Examiner* — Nathan Bowers
*Assistant Examiner* — Lydia Edwards
(74) *Attorney, Agent, or Firm* — Katten Muchin Rosenman LLP

(57) ABSTRACT

The invention resides in an apparatus for treatment of a substance. The apparatus has a substance tube for enabling a substance to be treated to pass in to the substance tube via the substance-inlet and out of the substance tube through the substance-outlet. The apparatus also has a cleaning chamber, wherein the substance tube is configured in fluid communication with the cleaning chamber to enable a substance to diffuse the permeable membrane between the substance tube and the cleaning chamber such that a substance can be substantially cleaned by a cleaner, the substance comprising blood or plasma and the cleaner comprising a cell culture. The substance tube is removably connectable with the cleaning chamber for inter-changeability or serviceability. The apparatus can further comprise a support compartment configured to connect to, or enclosing, the cleaning chamber, which functions to carry a fluid to substantially maintain the functionality of the cleaner.

17 Claims, 4 Drawing Sheets

(51) Int. Cl.
    *B01D 61/28*   (2006.01)
    *B01D 63/00*   (2006.01)
    *B01D 63/02*   (2006.01)
    *B01D 69/08*   (2006.01)
    *A61M 1/34*    (2006.01)
(52) U.S. Cl.
    CPC ........ *A61M 1/3489* (2014.02); *A61M 1/3496* (2013.01); *B01D 61/28* (2013.01); *B01D 63/00* (2013.01); *B01D 63/02* (2013.01); *B01D 67/00* (2013.01); *B01D 69/082* (2013.01); *Y10T 29/49723* (2015.01)
(58) Field of Classification Search
    CPC ........ B01D 63/02; B01D 65/02; B01D 67/00; B01D 69/082; Y10T 29/49723
    USPC ..................................................... 435/297.2
    See application file for complete search history.

(56) References Cited

U.S. PATENT DOCUMENTS 6,858,146 B1 * 2/2005 Myers .................... A61F 2/022
                                                        210/195.2
6,979,308 B1 * 12/2005 MacDonald et al. ...... 435/297.1

* cited by examiner

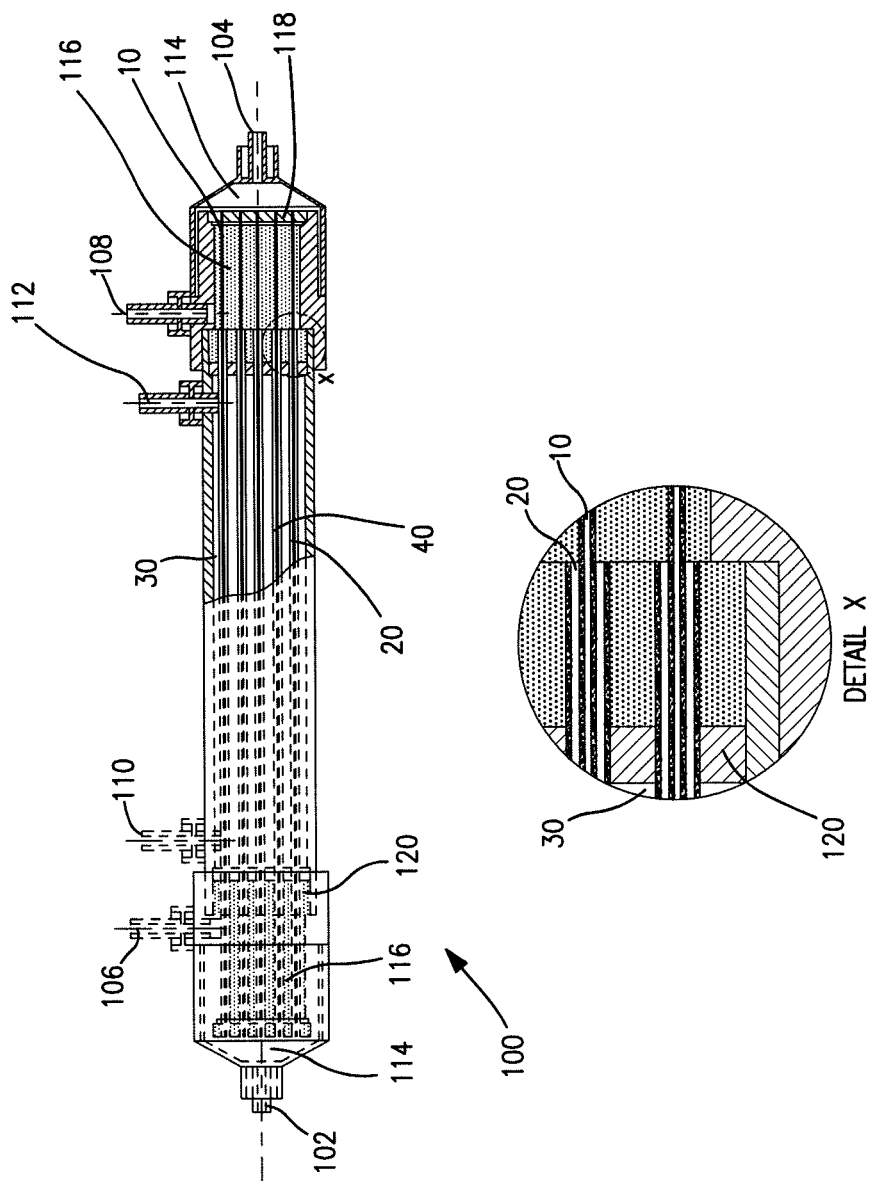

SERVICEABLE BIOREACTOR

This application claims priority from United Kingdom Patent Application No. 1210685.2, filed Jun. 15, 2012, entitled Serviceable Bioreactor, which is incorporated herein by reference.

FIELD OF THE INVENTION

The invention relates to a bioreactor and a method of assembling or servicing a bioreactor. The invention also relates to bioreactors in the field of biomedicine and biotechnology and, in particular, cell-based devices such as bioartificial organs that are configured to develop cell culture e.g. for a bioartificial liver device, such as a fiber in fiber (FIF) bioartificial liver (BAL) device.

BACKGROUND OF THE INVENTION

Fiber in fiber (FIF) bioartificial liver (BAL) devices are known. An example of which is described and discussed in a paper titled "Fiber in Fiber (FIF) bioartificial liver device: initial design and prototyping" by Hilal-Alnaqbi Ali, Basem Yousuf and Gaylor J. D. S. [Computer-Aided Design & Applications, 8(1), 2011, 99-109]. Devices are also known from and described in U.S. Pat. No. 6,582,955B and CN101199436.

Known designs consist of a conventional hollow fiber cartridge, which functions as a cell culture system, and a second hollow fiber placed in the lumen of the cartridge. Three zones or spaces are created. Known devices use guide plates to arrange the fibers the bioreactors. Unfortunately, the assembly of the bioreactor is complex. The assembly requires a body to be clamped vertically and a guide plate, having holes therein, placed in the recess in the upper end of the body. Hollow fibers are then threaded through the holes in the plate and kept static. A flowable silicone rubber elastomer is injected onto the plate and around the fiber walls to secure the fibers. Known bioreactors are, therefore, complex devices requiring delicate assembly techniques and are expensive to fabricate. Further, they are for one-time use because of nature of the assembly and the risk contamination.

SUMMARY OF THE INVENTION

It is against this background that the present invention has been made. This invention results from efforts to overcome the problems of known bioreactors. Other aims of the invention will be apparent from the following description.

The invention generally resides in an apparatus for culturing cell types. The apparatus is configured for treatment of a substance such as a cell culture (animal, human, plant, insect) e.g. human blood plasma, using a cleaner, such as a cell culture, a culture medium, blood or plasma e.g. bovine plasma, the apparatus having a tube through which a substance can flow, and a chamber in fluid communication the tube through which a cleaner can flow such that the substance can be substantially cleaned, and wherein the tube is removably connectable with the chamber for serviceability. The apparatus can have a compartment in fluid communication with the chamber through which a fluid, such as oxygen, can flow such that the functionality of the cleaner is substantially maintained.

Overall the invention can provide a serviceable bioartificial organ (e.g., liver, kidney, pancreas, thyroid, parathyroid, adrenal, etc.), such as a FIF bioreactor having a section for cells, perfusate and nutrient phases. Two or more separate sections can be provided for the cells and/or perfusate. The nutrient phases can be configured to pass adjacent to and/or through the perfusate. The blood or plasma to be treated passes adjacent a membrane in the apparatus, said membrane providing an interface that enables the blood or plasma to react to a material in an adjacent section of the apparatus. The perfusing function can be comparable to that provided by a natural organ.

The apparatus can have modules, or subcomponents that are serviceable to improve survivability and/or to adjust the capacity of the apparatus. The apparatus can function to provide cell therapy and oxygenation, cell therapy and blood/plasma dialysis, ultrafiltration or diafiltration. Other treatments are possible, such as the application of pharmacological agents.

The invention resides in a serviceable bioreactor in which a tube or channel for containing a substance to be cleaned is removably connected to a cleaning chamber. The tube and the chamber are in fluid communication via a membrane. The tube, chamber and/or compartment are can be connected and disconnected from each one another such that the apparatus can be taken apart and reassembled. In this way, one of the tube, chamber or compartment can be replaced or cleaned, thus avoiding waste, improving recycling and reducing cost. In one aspect, the invention resides in an apparatus for treatment of a substance, the apparatus having: a substance channel or tube configured to enable a substance to be treated to pass in to and out of the substance tube; a cleaning chamber connected to the substance tube, the cleaning chamber configured to enable a cleaner to pass in to and out of the cleaning chamber, wherein the substance tube is configured in fluid communication via a membrane with the cleaning chamber to enable a substance to diffuse or perfuse or permeate the connection between the substance tube and the cleaning chamber such that a substance can be substantially cleaned, or cleaned in part, by a cleaner, and wherein the substance tube is removable connectable with the cleaning chamber for inter-changeability or serviceability.

The substance channel or tube can have a substance-inlet and a substance-outlet in fluid communication with the substance tube for enabling a substance to be treated to pass in to the substance tube via the substance-inlet and out of the substance tube through the substance-outlet. The cleaning chamber connected to the substance tube can have a cleaner-inlet and a cleaner-outlet in fluid communication with the cleaning chamber for enabling a cleaner to pass in to the cleaning chamber via the cleaner-inlet and out of the cleaning chamber through the cleaner-outlet.

The tube can be shaped to increase the area of interface with the chamber and, by way of example, can have a helical shape along its axial length. The overall shape of the tube can be configured to maximise the surface are of the tube exposed to the interior of the cleaning chamber. The tube can also be configured to maximise the interaction between the substance passing through the tube and the cleaner in the cleaning chamber e.g. to maximise the flow across the surface of the tube.

The apparatus can further comprise a support compartment configured to connect to, or enclose, the cleaning chamber, the support compartment configured for enabling a support fluid to pass in and out of the support compartment, wherein the cleaning chamber is configured in fluid communication via a membrane with the support compartment to enable a fluid to diffuse, perfuse or permeate the connection between the cleaning chamber and a support compartment such that the fluid can substantially maintain the functionality of the cleaner.

The support compartment can have a support-inlet and a support-outlet in fluid communication with the support compartment for enabling a fluid to pass in to the support compartment via the support-inlet and out of the support compartment through the support-outlet.

By way of example, the cleaner passing through the cleaning chamber may be oxygen dependent, such as a cell culture, blood or plasma. Depending on the configuration of the apparatus, some of the cells of the cell culture, blood or plasma may die without support as they pass through the cleaning chamber. The support chamber, therefore, is in fluid communication via a membrane with the cleaning chamber to supply a support fluid, such as oxygen, directly to the cleaner. Preferably, the support fluid is a biological support fluid.

The substance tube and/or the cleaning chamber can be removably connectable, or coupleable to the support compartment.

The connection, or coupling, between the or each components part of the serviceable BAL can be an interference-fit for inhibiting liquid or fluid leakage from the apparatus. Said coupling is a serviceable connection or joint between the components of the apparatus and can be a screw-fit, compression fit, pressure-fit, snap fit or bayonet-fit. Additional components, such as a mechanical compression band, or clip, that can be tightened around the perimeter of the units, can be used to compliment the connection. One or more sealing elements, such as a washer or grommet, can be used to provide or improve the connection.

The apparatus can have a manifold, or substance store, at an end of the substance tube, or at both ends. The manifold functions to collect a substance received from the substance inlet/outlet before said substance passes in/out of the tube. A manifold can connect to a plurality of tubes, chambers or compartments. A manifold can make several connections within the same assembly or service action. The manifold can simplify the serviceability of the apparatus by reducing the number of connections or couplings required between the different components of the apparatus.

The substance tube can have a web configured to form the substance store at each end of said tube. Said tube can be mounted on said web such that a portion of the substance tube passes through the web at the mounting point, and wherein substance tube is removably connected to at least one web. The web can be formed of a disk-like structure having a plurality of holes, with a substance tube passing through, or in to, each hole.

The apparatus can have a plurality of substance tubes. A web can be configured at each end of the plurality of said substance tubes. The connection between the substance tube and the web can be a push-fit. The web can be configured to separate the substance store from the cleaning chamber when the substance tube is connected thereto.

The apparatus can have a manifold, or cleaner store, at an end of the cleaner chamber, or at both ends. The manifold functions to collect a cleaner received from the substance inlet/outlet before said cleaner passes in/out of the chamber. The cleaner chamber can have a web configured to form the cleaner store at each end of said tube. Said chamber can be mounted on said web such that a portion of the cleaner chamber through the web at the mounting point, and wherein cleaner chamber can be removably connected to at least one web. The cleaner store can be configured in fluid communication with a plurality of cleaner chambers.

Alternative arrangements of the apparatus can have different interfaces or connections between the tube and the chamber. By way of example there can be two or more surfaces of the tube, chamber or compartment. The number of surfaces, and their configuration, can be optimised to maximise the fluid connectivity between the tube, chamber and compartment.

The invention can additionally or alternatively be implemented in alternative configurations that are more robust. By being more robust, and less delicate, the handling and serviceability can be improved. Further, the life of the serviceable apparatus can be increased. The increase in robustness can be achieved by the configuration of the tube, chamber and compartment.

The cleaning chamber can be configured to surround or enclose the substance tube and/or the support compartment. Where the cleaning chamber encloses the support compartment the walls of the support compartment has, at least in part, a membrane and the surface are of the support compartment is configured to support the cleaner material. The support compartment can be coiled and/or have a helical form in an axial direction.

The substance tube can be substantially circular in cross section. The substance tube, in cross-section, can have two faces, or three or more faces. If the substance tube has two faces it can, by way of example, have a cross-sectional profile comparable to that of an optical lens having two convex faces. If the substance tube has three faces it can, by way of example, have a cross-sectional profile comparable to a triangle, such as an equilateral triangle.

The cleaning chamber can be substantially circular in cross section. The cleaning chamber, in cross-section, can have two, or three or more faces. The support compartment can be substantially circular in cross section. The support compartment, in cross-section, can have two, or three or more faces. The interfacing surfaces between the tube, chamber and compartments, whether directly connected or in fluid communication, are configured to maximise the surface area therebetween. At least a portion of the cross-section profile of the wall of the support tube and/or cleaning chamber can be substantially wave-shaped. The wave shape can be sinusoidal, triangular or square.

The cleaning chamber, in cross-section, can have one face configured to engage with a reciprocal face of the substance tube, and another face configured to have a maximum interface.

The shape of tube, chamber or compartment can take on a variety of forms such that the cross-sectional profile can be irregular, asymmetrical, or symmetrical. By way of example, the cross-sectional profile can be hexagonally shaped.

Similarly, the shape of the tube, chamber or compartment can take on a variety of forms along the longitudinal length to be irregular, or regular. By way of example, the tube, chamber or compartment can have a wave-shaped profile, such as a sinusoidal profile, along its length. The tube, chamber or compartment can have a helical form. A convective flow configuration can be used. Alternative flow configurations can be implemented and the flow direction in one tube or chamber can be in the opposite direction from an adjacent tube or chamber. To be clear, the flow configuration can be the same, or different between the tubes, and the flow can be a convective flow or a dead-end-flow. By way of example, the flow in the tube 10 and the chamber can be convective, and in the same direction, while the compartment has a dead-end flow. Note that the arrangement of the invention is not limited to the arrangement and functionality described above i.e. that the tube carries a substance, the chamber carries a cleaner and the compartment carries a support material. The apparatus of the invention is flexibly configurable such that any one of the tube, chamber or compartment can perform the function of the other. By way of example, the apparatus can be configured such that the substance to be treated can pass in to the support compartment, the cleaner can be configured to pass in to the cleaning chamber (as originally intended) and the support fluid can pass in to the substance tube.

Not only is the apparatus serviceable, but it is configured to achieve acceptable cell viability and functions. The mass transport (by diffusion or convection) from a nutrient or gas supply source to the cells is important and the invention aims to improve the mass transport within the apparatus. Oxygen is important for cell viability and function and the invention provides an improved configuration to overcome the limitation of mass transport (i.e. oxygen) which occurs in known devices. In view of these and other variants within the inventive concept, reference should be made to the appended claims rather than the foregoing specific description in determining the inventive concept.

BRIEF DESCRIPTION OF THE DRAWINGS

In order that the invention may be more readily understood, reference will now be made, by way of example, to the drawings in which:

FIG. 2 is a longitudinal cross-sectional view of an apparatus according to one aspect of the invention showing the structure of the apparatus having inlet and outlet ports to three discrete compartments, wherein each compartment is removable connectable from the other;

Although the invention relates to a bioreactor and, in particular a serviceable bioreactor and a method of servicing a bioreactor the invention will be described, by way of example, in relation to a fiber in fiber (FIF) bioartificial liver (BAL) device.

DESCRIPTION OF THE PREFERRED EMBODIMENT

A FIF BAL device is configured to support acceptable cell viability and cell functionality. The mass transport (by diffusion or convection) from a nutrient or gas supply source to the cells is important and one of the aims of the invention is to improve the mass transport within the apparatus. Oxygen is important for cell viability and function and the invention provides an improved configuration to overcome the limitation of mass transport (i.e. oxygen) which occurs with known devices.

The FIF device can comprise a hollow fibre inside another hollow fibre bioreactor to accommodate liver cells (hepatocytes). The configuration mimics the liver acinus since it can supply oxygen at physiological partials pressures. In this configuration, the hepatocytes reside in the cleaning chamber.

Figure 1:
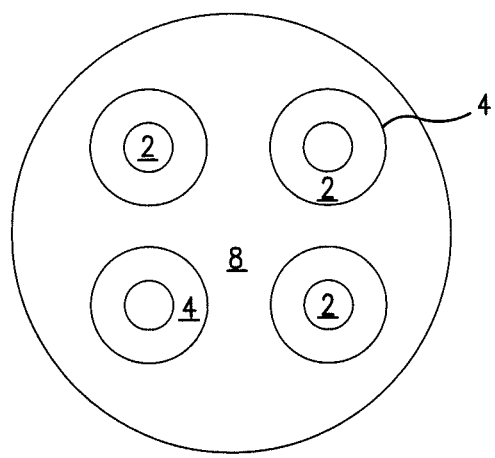
FIG. 1 is a cross-section of a mid-section of known fiber in fiber (FIF) bioartificial liver (BAL) device, having a number of tubular fibers, each arranged within a larger fibrous tube, which are located in a larger tube.

Referring to FIG. 1, a first compartment 2 is located, coaxially, within a second compartment 4 to provide a fibre in fibre (FIF) unit 6. A number of FIF tubes 6 are arranged within a third compartment 8. The first compartment 2, second compartment 4 and third compartment 8 are cylindrical. The walls of the FIF unit 6 comprise a membrane 9.

The first compartment 2, second compartment 4 and third compartment 8 of FIG. 1 are analogous, respectively, with a substance tube 10, a cleaning chamber 20 and a support compartment 30 as shown in FIG. 2. The or each wall of the tube 10 or chamber 20 can be formed, at least in part, by the membrane 9. The properties of the membrane on the or each wall can differ.

In use, a patient's blood would be introduced into the tube 10 of the apparatus of FIG. 2 and a chemical species transported through the membrane into the chamber 20, either by diffusion or convection, which carried bovine plasma. There are at least two ways to use chamber 20, as follows:

(1) If the membrane excludes all species (mid cells) of a molecular weight (MW) >70000, then the membrane acts as immunological barrier between the cells cultured in the chamber 20 and the blood in the tube 10. Hepatic failure toxins which are not protein bound would diffuse into the chamber 20 for detoxification. Transformed species may diffuse back into the tube 10.

(2) If the membrane is configured as a plasmapheresis membrane, plasma separated from whole blood in the tube 10 will be convected into the chamber 20. Assuming cells are present in the chamber 20, protein-bound toxins will be detoxified and returned by back convection of plasma into the tube 10 together with synthesised products. Plasma is reunited with the primary blood flow in the tube 10 and whole blood exits the tube.

The membrane between the cell culture and the patient's perfusate can be configured to 1) maximise the function of the cells by increasing the density of cultured cells, 2) promote effective exchange of substances, 3) provide cell anchorage, 4) reduce immunological hazards and 5) exhibit sieving properties.

Using the second way described above may compromise the oxygen requirements of the cells passing through the chamber 20. While the oxygen requirement of the cells can be met more easily with blood, plasma perfusion would require oxygenation and a very high flow rate. These requirements make the procedure more complicated. A further consideration is the duration over which plasma separation can be effectively achieved before concentration polarisation renders the membrane ineffective. Thus, the treatment time might be dictated by membrane fouling.

The support compartment 30 can solve the problem of oxygen delivery requirements to the cells in the chamber 20 if it is configured as a pure gas supply space with the membrane of the chamber 20 configured as a gas permeable hydrophobic membrane. Preferably, the tube 10 should not be more than 200 µm in radius in order to provide better nutrient and oxygen transport. A convective flow configuration can be used.

The walls of the tube 10 or chamber 20 can have reinforcement to inhibit movement or collision between the membrane wall of the tube and the membrane wall of the chamber 20. This could affect the growth, life or even the function of the cells. Additionally or alternatively, the position and separation of the tubes and chambers is controlled along the length of the tube/chamber to maintain uniform separation. The shape of the tube and/or chamber can be used to inhibit movement.

If hepatocytes (cells of the liver) were embedded with a gel/nutrient medium they could be circulated inside the chamber 20 to nourish and maintain the hepatocytes in culture. It can be circulated counter current to the patients' perfusate. Thus, the toxins and metabolites produced during liver disease could diffuse out of the highly permeable hollow fibre along a concentration gradient. The metabolic end products would then be excreted into the chamber 20 along the concentration gradient and be removed by the circulating nutrient medium. Concurrently, essential proteins and factors produced by the hepatocytes in the chamber 20 would diffuse along a concentration gradient through the membrane wall of the tube 10 and enter the patient's perfusate in tube 10.

The semi-permeable hollow fibre membrane of the tube 10 can protect the cultured hepatocytes from the body's immune system and can protect the patients' blood from the toxins coming from xenogenic cells if such cells were selected. Cell to cell contact would be addressed for long-term stability of hepatic functions. The apparatus can be configured to increase the removal of ammonia and albumin synthesis, as well as sufficient oxygen transfer.

The compartment 30 is formed by a jacket 31 housing the tube 10 and chamber 20 assembly and allows a fluid (i.e., liquid or gas) culture medium to pass therethrough to assist in maintaining the hepatocytes, keeping them alive and functioning for longer within chamber 20.

The compartment 30 can be used as receiver of lower molecular weight substances, which have been produced by the cell metabolism. These substances will be transported by diffusion from the chamber 20 into the compartment 30 through a low molecular weight cut off membrane. The removal of these low molecular weight substances from the compartment 30 could be supported by transport of soluble nutrients in a cell culture medium introduced into compartment 30.

Alternatively, the compartment 30 can be used for circulating a gas mixture (containing $O_2$, $N_2$ and $CO_2$). Using the compartment 30 in this manner would solve the oxygen-limiting problem suffered by known bioartificial liver devices in that it provides a parallel pathway for $O_2$ and $CO_2$ removal from the chamber 20. This integral oxygenation can inhibit the axial gradients and oxygenate the media in the chamber 20 to the levels similar to those found in the periportal region of the liver i.e. 70 mm Hg.

If the compartment 30 is used as a gas supply, the membrane wall of chamber 20 should have the characteristics of gas-permeable membranes, such as microporous and non-microporous membranes as oxygenation membranes.

Each tube 10 located in a chamber 20 forms a Fibre in Fibre unit 6, 40. In practice a FIF BAL contains a plurality of units 40, each unit having a single tube 10 within a chamber 20.

Note that the support compartment is optional, depending on the application. If required, a support compartment 30 can be configured to be connected to a cleaning chamber 20. Additionally or alternatively a support compartment 30 can be configured to enclose and/or pass through a cleaning chamber 20. An apparatus having a tube 10 and chamber 20 can, alternatively, be placed in a suitable environment such that a dedicated compartment is not required, for example an oxygenated room.

Returning back to FIG. 2, apparatus 100 has a substance-inlet 104 and a substance-outlet 102 configured in fluid communication with the substance tube 10 for enabling a substance to be treated to pass in to the substance tube via the substance-inlet and out of the substance tube through the substance-outlet. A cleaner-inlet 106 and a cleaner-outlet 108 are configured in fluid communication with the cleaning chamber 20 for enabling a cleaner to pass in to the cleaning chamber via the cleaner-inlet and out of the cleaning chamber through the cleaner-outlet. A portion of the wall of the substance tube 10 is configured in fluid communication via a membrane with the cleaning chamber to enable a substance to diffuse, perfuse or generally pass through to a controlled degree the connection between the substance tube and the cleaning chamber such that a substance can be substantially cleaned by a cleaner.

As described above, the apparatus can have a support compartment 30 having a support-inlet 110 and a support-outlet 112 in fluid communication with the support compartment 30 for enabling a fluid to pass in to the support compartment via the support-inlet and out of the support compartment through the support-outlet. The cleaning chamber is configured in fluid communication via a membrane with the support compartment to enable a fluid to diffuse, perfuse or generally pass through to a controlled degree between the cleaning chamber 20 and the support compartment 30 such that the fluid can substantially maintain the functionality of the cleaner.

The apparatus 100 of the invention can be configured such that each of the substance tube 10, cleaning chamber 20 and support compartment 30 has a single inlet and a single outlet. Practically, however, the inlet of the tube 10 and/or the chamber 20 can be connected to a plurality of tubes or chambers. This connection can be achieved by using a manifold. The configuration of the apparatus as shown in FIG. 2 is one example of a single inlet providing connection to a plurality of tubes or chambers.

The substance-outlet 102, feeds into a substance store 114 such that a substance can be centrally collected and distributed between the substance tubes 10. As a substance passes out of the substance tubes 10 it passes into another substance store at the opposite end of the tube before passing out of the substance-outlet. Similarly, there is a cleaner store 116 at each end of the cleaning chamber. The stores 114, 116 function as manifolds. The manifolds can be integral with the apparatus.

The substance tubes 10 are held at each end by a web 118 configured to form the substance store 114. The web forms a barrier between the substance store and the cleaner store 116. Similarly, the cleaning chambers are held in a web 120 to separate the substance store from the cleaning chamber when the substance tube is connected thereto. When the Fibre in Fibre unit 40 passes through a support compartment 30 the web 120 separates the cleaner store 116 from the support compartment 30.

Detail X of FIG. 2 shows a chamber 20 passing through a web 120, in which it is mounted, which separates the store 116 from the compartment 30. Tubes 10 are shown passing through the chamber 20.

Known FIF BAL devices are disposable, and for one-time-use only. The apparatus of the invention, however, is serviceable. The substance tube 10 is removably connectable to the cleaning chamber 20 such that a soiled or contaminated tube 10 can be replaced. Similarly, the chamber 20 can be removably connected with the support compartment 40.

Figure 3:
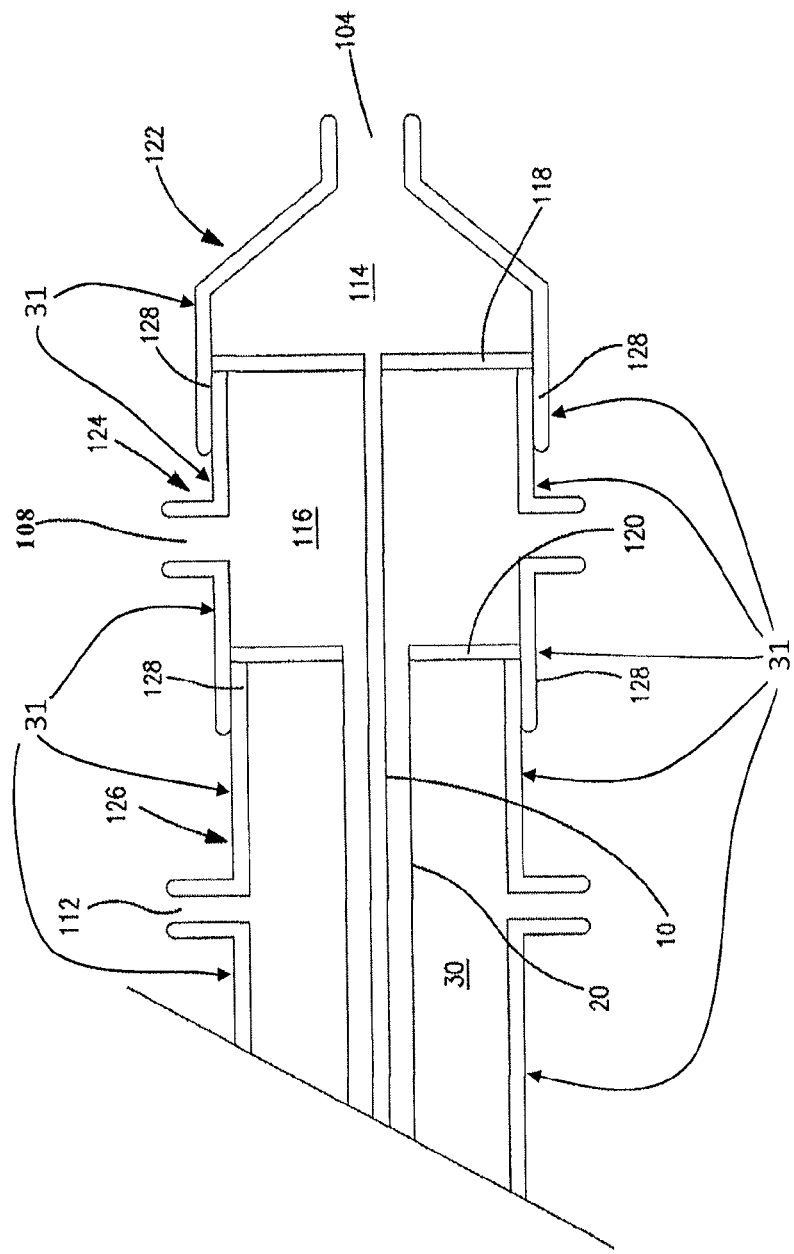
FIG. 3 shows an end portion of an apparatus according to the invention indicating, by way of example, the connection points, coupling points or interfaces between the compartments.

The apparatus of FIG. 2 demonstrates an embodiment of the invention and like components are referred to with like reference numerals in FIG. 3 that, by way of example, is used to describe the structural elements of the device that enable the apparatus 100 to be serviced.

The illustration of FIG. 3 shows the end portion of three units, namely: a substance unit 122, having a substance inlet and outlet 104, 102, a substance store 114 forming a manifold defined by an upper, lower and a lateral wall, as viewed, of the unit and a web 118, and a substance tube 10 connected to and passing through the web 118; a cleaning unit 124, having a cleaner inlet and outlet 106, 108, a cleaner store 116 forming a manifold defined by an upper and lower wall as viewed, a web 120 and a cleaning chamber 20 connected to and passing through the web 120; and a support unit 126 forming a support compartment 30 in the form of a tube having open ends, and a support inlet and outlet 110, 112. The ends of the apparatus shown in FIG. 3 are, by way of example, a mirror image of the opposite end of the apparatus.

Note that the cleaning unit 124 would, as a stand-alone component, be open on one side to create a recess that is configured to be closed off by the substance unit 122 to provide the store or manifold 116 and, by way of example in FIG. 3, it is the web that functions to close it off. Similarly, the web 120 of the cleaning unit is configured to close the ends of the support compartment 30 the cleaning unit.

The web 118 and walls of the substance unit 122 provide a socket area, or recess 128. The socket 128 is configured to receive the walls of the open end of the cleaning unit 124 and create an enclosed cleaner store 116. Similarly, the web 120 and walls of the cleaner unit 124 provide a socket area, or recess 128. The socket 128 of the cleaner unit is configured to receive the walls of the open end of the support compartment 30. The socket enables the component of the apparatus to be assembled, and taken apart again for servicing.

The sockets shown in FIG. 3 are configured, by way of example, such that the wall of the support unit 126 has an interference-fit within the socket 128 configured to inhibiting liquid or fluid leakage from the apparatus from the support compartment 30. This type of connection is not permanent and enables the device to be serviceable.

The serviceable connection or joint between the substance unit 122, cleaning unit 124 and support unit 126 can be configured to inhibit or prevent liquid or fluid leakage from the joints between the apparatus in a number of ways using: screw-fit, where the units are screwed together; compression fit, where an intermediate components functions, upon applied pressure, to form a seal; bayonet-fit; a mechanical band that can be tightened around the perimeter of the units; snap-fit; or a combination thereof. One or more seals can be used in forming the connection.

The or each web 118, 120 can be rotatably mounted within the units 122, 124 to allow to walls of the enclosure and socket 128 to be moved independently of the web and the tube 10 and chamber 20. To be clear, the tubes 10 and chambers 20 can be movable independently of the manifolds and/or walls of the units 122, 124, 126.

Assembling the apparatus can be achieved in number of ways depending on the type of connection between the units and whether sub-assemblies are used. By way of example, the assembly of a complete apparatus (only one end of which is shown in FIG. 3) will be described as follows.

A web 120 is positioned in the main body of one end of a cleaning unit 124, having a port 108, and located at one end of the apparatus. In this example, the apparatus is substantially cylindrical and the web is disc-like with a port located therein for receiving the end of a cleaning chamber 20. At one end the cleaning chamber 20 is secured in the port of the web 120. The other end of the chamber 20 is secured in the port of a web 120 located in the body of another cleaning unit 124 located at the other end of the apparatus.

If the apparatus is configured with a support compartment 30, the chamber 20 is first fed through the body of the support unit 126 and connected to the web 120 located in the body of another cleaning unit 124 located at the other end of the apparatus. By way of example, the chamber 20 can be connected to the port of the web 120 using a push-fit. Assembled, the cleaning chamber 20 is secured between cleaning units 124 at either end of the apparatus. If a support compartment 30 is used then the chamber 20 passes through the core of the support unit 126 and the ends of the unit 126 are secured in the sockets 128 located on the cleaning unit at either end of the apparatus.

A web 118 is positioned in the main body of one end of a substance unit 122, having a port 104, and located at one end of the apparatus. The web is disc-like with a port located therein for receiving the end of a substance tube 10. At one end the tube 10 is secured in the port of the web 118. The other end of the tube 10 is fed through the chamber 20 and secured to the web 118 located in the port of a web 118 located in the body of the other end of the substance unit 122 located at the other end of the apparatus. By way of example, the tube 10 can be connected to the port of the web 118 using a push-fit.

The connection between the chamber 20 or tube 10 and the web can be a push-fit. The chamber 20 or tube 10 can, at least in part, have reinforcement to ease the assembly process and/or connection with a web, and to inhibit bending or flexing of the chamber 20 or tube 10. The apparatus can be provided with a number of intermediate webs positioned between the ends of the apparatus to control the cross-sectional position of the chamber along the length of the apparatus.

Servicing the apparatus requires reversing the above-mentioned steps.

In the above example, a single substance tube 10 is coaxially aligned to pass through a cleaning chamber 20, which is in turn arranged to pass through a support compartment 30. Other arrangements of the tube 10, chamber 20 and compartment 30 are possible using the assembly techniques applied herein. The apparatus can have a plurality of chambers 20, with each chamber 20 having a single tube passing coaxially therethrough. Alternatively, the or each chamber 20 can have a plurality of tubes passing therethrough. Additionally or alternatively, the support compartment 30 can be configured to pass through the cleaning chamber 20.

In one aspect of the invention the tube, chamber and compartment are coaxial and a single tube or plasmapheresis hollow fibre is configured within a single chamber or oxygenation hollow fibre to provide a functional element of the FIF bioreactor.

Figure 4A:
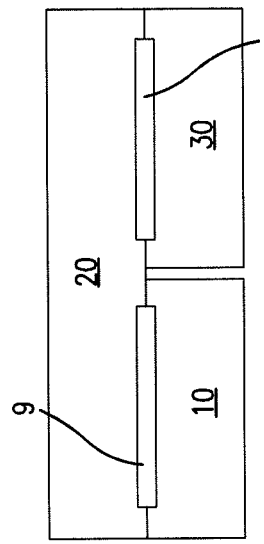
FIGS. 4a and 4b show, in cross-section, alternative configurations of the compartments according to the invention.
Figure 4B:
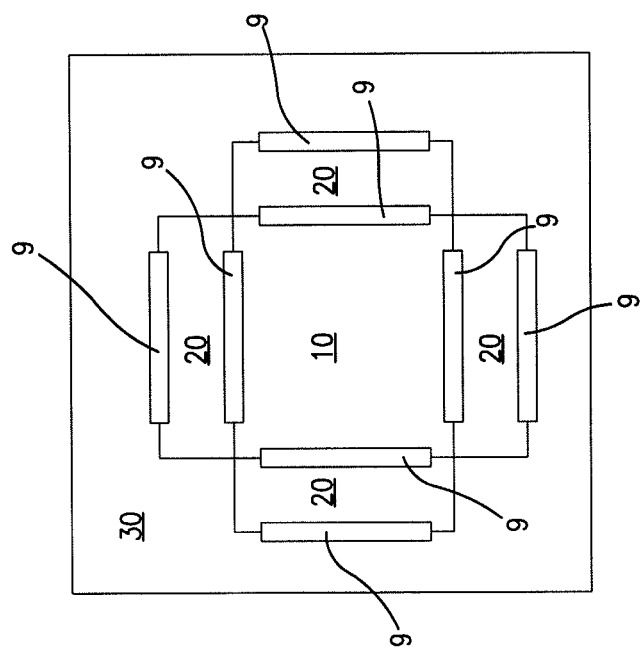

The tubes of the apparatus are not, however, limited to being cylindrical. The cross-sectional profile of the substance tube 10, cleaning chamber 20 and support compartment can be quadrilateral in shape, and can be rectangular, in cross-section, as shown in FIGS. 4a and 4b. To be clear, the tube, chamber and compartment can be cuboid, or box-shaped. FIG. 4a shows an apparatus having a tube 10 connected to a chamber 20. The chamber 20 is connected to a compartment 30. A membrane 9 separates is configured between the tube and chamber, and the chamber and the compartment such that there is fluid communication therebetween such that apparatus functions in the same manner, by way of example, as described above for FIG. 2. The apparatus of FIG. 4a is serviceable. The tube 10 can be replaceably removed from the chamber 20. Similarly, the compartment 30 can be replaceably removed from the chamber 20. By way of example, the connection therebetween is a sliding bayonet connection.

FIG. 4a can be described as a flat-plate configuration. In other words, the tube, chamber and compartment are substantially planar. The planes of the tube, chamber and compartment can be substantially parallel to each other.

FIG. 4b shows, by way of example, in cross-section, a square-shaped tube 10 having chamber 20 connected on each of its four sides, having a membrane 9 therebetween. The tube-chamber assembly is optionally located within a compartment 30.

The invention is not limited to a fiber-in-fiber arrangement and the communication between the tube, chamber and compartment can achieved through alternative arrangements. All, or at least a part, of the wall between the tube 10 and the chamber 20, and between the chamber 20 and the compartment 30, has a membrane 9.

The tube, chamber and compartment are aligned coaxially. Multiple tubes and/or chambers can be arranged multicoaxially. The inlets and outlets can be configured on the ends of the apparatus, and manifolds can be provided for the inlets and outlets.

The shapes of the tube 10, chamber 20 and compartment 30 can be a combination of shapes according to the application of the apparatus. Differing shapes can be configured to increase strength to inhibit flexing along the axial length of the apparatus. Some shapes can increase the surface area of the tube 10 or chamber 20 for a given volume. Some shapes can also be advantageous for serviceability requirements by improving the ease at which one component can be removably connected to another. By way of example, in cross section, a portion or section of the connection between the tube 10, chamber 20 and compartment 30 can have a wave-shaped profile to increase the surface area therebetween.

Different configurations of apparatus allow for different membrane types to be used. By way of example, high permeability membranes allow faster diffusion of molecules and, consequently, a better alimentation of the cells in nutrients. To avoid the deterioration of the cells by the immunological system of the patient's perfusate, a limitation of the membrane pore size needs to be observed. As the molecular weight of the plasma proteins increase it becomes more difficult for them to travel through the membrane. The apparatus can be configured to inhibit membrane fouling (concentration polarisation) by plasma proteins. The degree of fouling is influenced by the flow conditions (i.e. shear rate) and configuration (i.e. cross flow) within the device. Baffles can be used to stimulate movement or flow within the apparatus.

Further, the solute mass transfer in a membrane-based bioreactor depends on a number of factors including the membrane type, the bioreactor geometry and the location of the compartments. Internally, the phenomenon responsible for mass transport is diffusion, convection, or a combination thereof.

Different shape combinations are explained, by way of example, using the cross-sectional profiles of the apparatus.

Figure 5A:
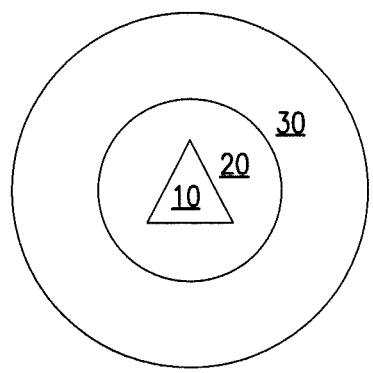
FIGS. 5a and 5b show, in cross-section, alternative configurations of the compartments shown in FIG. 2 according to the invention.
Figure 5B:
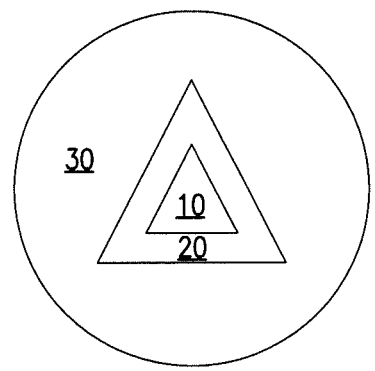

FIGS. 5a and 5b show arrangements wherein the walls of the tube 10 and the chamber 20 are in fluid communication, but not connected, along the axial length of the apparatus. The tube 10 described above has been described as being cylindrical and having a single wall. In the configuration of FIG. 5a, the tube 10 has 3 sides while the chamber 20 and compartment 30, in cross-section, is circular and has one side. The tube can have two or more sides. The chamber 20 too has been described above as being cylindrical and having a single wall and in the configuration of FIG. 5b, both the tube 10 and the chamber 20 has two or more sides and are shown having triangular structures in cross-section, while the compartment is circular. By having two or more sides along at least a portion of the axial length flexing of the tube and/or the chamber can be inhibited.

Figure 6A:
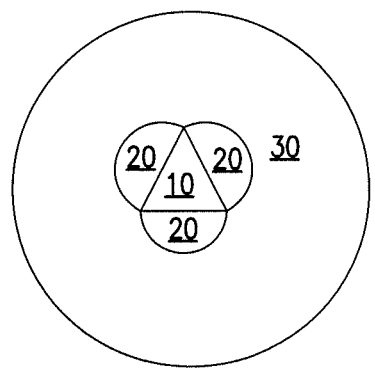
FIGS. 6a to 6b show, in cross-section, alternative configurations of the compartments shown in FIG. 4 according to the invention.
Figure 6B:
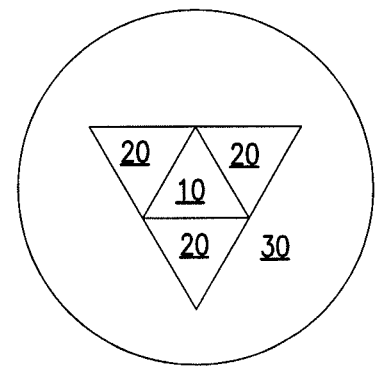

FIGS. 6a and 6b show cross-sectional arrangements wherein the tube 10 and the chamber 20 are connected along one axial face along at least a portion of the axial length of the apparatus. In the configuration of FIG. 6a, the tube 10 has a triangular structure and there are three chambers 20, each having two sides—one side engages with, and is in fluid communication with the tube 10 via a membrane while the other is hemispherical and in fluid communication with the compartment 30. In FIG. 6b the tube has three sides and a chamber is connected to each side—one side engages with the tube 10 while the other two form the triangular shape of the chamber.

Figure 7:
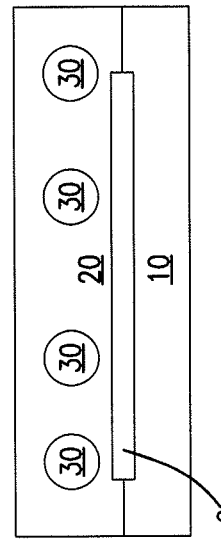
FIG. 7 shows, in cross-section, an alternative configuration of the compartments according to the invention.

FIG. 7 shows an alternative arrangement of FIG. 4a, wherein a number of support compartments 30, that are circular in cross-section, pass through the cleaning chamber 20 rather than being configured to pass adjacent the chamber 20.

The configurations of FIGS. 4a to 7 can be adapted to have a plurality of tubes 10 and/or chambers 20. Connections can be made to the tubes or chambers directly, or via a manifold or substance store 114 and/or a cleaner store 116.

The terms tube, chamber and compartment have been used throughout this application. Respectively, they can alternatively be named as the first chamber (tube), second chamber (chamber) and third chamber (compartment). In the above examples a convective flow configuration can be used. Alternative flow configurations can be implemented and movement of the substances in the apparatus can be optimised with baffles.

In view of these and other variants within the inventive concept, reference should be made to the appended claims rather than the foregoing specific description in determining the inventive concept. The present invention is not to be limited in scope by the specific aspects and embodiments described herein. Indeed, various modifications of the invention in addition to those described herein will become apparent to those skilled in the art from the foregoing description and accompanying figures. Moreover, all aspects and embodiments described herein are considered to be broadly applicable and combinable with any and all other consistent aspects and embodiments, as appropriate.

Various publications are cited herein, the disclosures of which are incorporated by reference in their entireties.

The invention claimed is:

1. An apparatus for treatment of a substance, the apparatus including:
   a substance tube configured to enable a substance to be treated to pass in and out of the substance tube;
   a cleaning chamber which, in an assembled condition of the apparatus, is connected to the substance tube through a permeable membrane, the cleaning chamber configured to enable a cleaner to pass in and out of the cleaning chamber, wherein the substance tube is configured in fluid communication with the cleaning chamber via the permeable membrane to enable said substance to perfuse the permeable membrane between the substance tube and the cleaning chamber such that said substance can be substantially cleaned by the cleaner, the substance consisting of blood or plasma and the cleaner comprising a cell culture, and wherein the substance tube is removably connectable with the cleaning chamber such that the apparatus can be taken apart and reassembled.

2. The apparatus according to claim 1, the apparatus further comprising a support compartment configured to be connected to, or enclosing, the cleaning chamber, the support compartment configured to enable a biological support fluid to pass in and out of the compartment, wherein the cleaning chamber is configured in fluid communication with the support compartment via a permeable membrane to enable said biological support fluid to perfuse the connection between the cleaning chamber and the support compartment such that the biological support fluid can substantially maintain the functionality of the cleaner.

3. The apparatus according to claim 2, wherein the substance tube is removably connectable to the support compartment.

4. The apparatus according to claim 3, wherein the cleaning chamber is removably connectable to the support compartment.

5. The apparatus according to claim 4, wherein the coupling between the or each connection is an interference-fit for inhibiting liquid or fluid leakage from the apparatus.

6. The apparatus according to claim 5, wherein the apparatus has a substance store at each end of the substance tube, wherein the substance store functions to collect the substance received from the substance inlet/outlet before said substance passes in/out of the tube.

7. The apparatus according to claim 1, wherein the cleaning chamber is configured to surround or enclose the substance tube.

8. The apparatus according to claim 7, wherein the cleaning chamber is configured to surround or enclose the support compartment.

9. The apparatus according to claim 8, wherein the substance tube is substantially circular in cross section.

10. The apparatus according to claim 9, wherein the cleaning chamber is substantially circular in cross section.

11. The apparatus according to claim 9, wherein the support compartment is substantially circular in cross section.

12. Apparatus for culturing cell types, comprising an apparatus according to claim 1.

13. The Apparatus according to claim 1, wherein the removable connection of the substance tube to the cleaning chamber permits the substance tube and the cleaning chamber to be replaced or cleaned.

14. The apparatus according to claim 1, wherein the apparatus further includes:
    a jacket for housing the substance tube and the cleaning chamber; and
    removably connecting means including:
    (a) first removably connecting means removably connectable between the substance tube and the jacket;
    (b) second removably connecting means removably connectable between the cleaning chamber and the jacket;
    wherein the first and second removably connecting means removably connect the substance tube, the cleaning chamber and the jacket to one another, thereby to removably connect the cleaning chamber in fluid communication with the substance tube in the assembled condition of the apparatus, and wherein the first and second removably connecting means are configured to permit the substance tube and the cleaning chamber to be connected and disconnected from one another to provide for said taking apart and the reassembly of the apparatus.

15. The apparatus according to claim 14, wherein the first and second removably connecting means are reusable so as to permit the apparatus to be taken apart and reassembled a plurality of times.

16. The apparatus according to claim 14, wherein the first removably connecting means is in the form of at least one web and wherein the substance tube is removably mounted to the web such that a portion of the substance tube passes through the web at a mounting point, the web being configured such that a connection between the web and the substance tube and a connection between the web and the jacket is an interference fit for inhibiting liquid or fluid leakage from the apparatus.

17. The apparatus according to claim 14, wherein the second removably connecting means is in the form of at least one web and wherein the cleaning chamber is removably mounted to the web such that a portion of the cleaning chamber passes through the web at a mounting point, the web being configured such that a connection between the web and the cleaning chamber and a connection between the web and the jacket is an interference fit for inhibiting liquid or fluid leakage from the apparatus.

* * * * *